United States Patent
Dirbas

(10) Patent No.: US 6,182,047 B1
(45) Date of Patent: Jan. 30, 2001

(54) MEDICAL INFORMATION LOG SYSTEM

(75) Inventor: Frederick Mark Dirbas, Menlo Park, CA (US)

(73) Assignee: Software for Surgeons, Menlo Park, CA (US)

( * ) Notice: Under 35 U.S.C. 154(b), the term of this patent shall be extended for 0 days.

(21) Appl. No.: 08/458,905

(22) Filed: Jun. 2, 1995

(51) Int. Cl.[7] .................................................. G06F 159/00
(52) U.S. Cl. ................................................................ 705/3
(58) Field of Search .................................... 364/401, 406, 364/408; 395/140, 157; 705/1–3, 4; 707/110, 100, 200

(56) References Cited

U.S. PATENT DOCUMENTS

| 4,878,175 | 10/1989 | Norden-Paul et al. | 364/401 M |
| 5,077,666 | 12/1991 | Brimm et al. | 364/408 |
| 5,262,943 | 11/1993 | Thibado et al. | 364/401 M |
| 5,325,293 | * 6/1994 | Dorne | 705/2 |
| 5,327,341 | 7/1994 | Whalen et al. | 364/401 M |

FOREIGN PATENT DOCUMENTS

0457000A2   11/1991   (EP).

OTHER PUBLICATIONS

Wyatt, "Clinical Data Systems, Part 3: Development and Evaluation", Lancet, V344, N8938, P1682(7), Dec. 17, 1994, Dialog File 148, Accession No. 07620766.

Ornstein Et Al. "The Computer–Based Medical Record: Current Status", Journal of Family Practice, v35, N5, 556(10), Nov. 1992, Dialog File 149, Accession No. 01374326.

* cited by examiner

Primary Examiner—Frantzy Poinvil
(74) Attorney, Agent, or Firm—Townsend & Townsend & Crew LLP

(57) ABSTRACT

A computer system (100) for providing a medical information log system (202). A mouse (107) and/or a keyboard (106) is used to input data (400) for various medical log entries. These log entries are associated with a medical visit, and they contain information related to the doctor (1020) and the type of said medical visit (1040). Each medical visit has only one log entry associated with it. The inputted data is stored within an organized database located in the computer's memory (103, 108). The computer's controller (101) is used to track the inputted data for various desired information. This information can be used for record keeping, outcome analysis, research, teaching, quality assurance, and/or billing. The inputted data is displayed on display (105) when desired.

5 Claims, 18 Drawing Sheets

Microfiche Appendix Included
(1 Microfiche, 74 Pages)

Data Entry return to main menu · new entry · case summary

| | |
|---|---|
| Patient Name (F M L) | Initials / Date |
| Patient DOB, Age / MR # / Sex ○M ○F | press here for today's date ○ |
| Operative classification for RRC coding [Select] | CPT Code |
| ← ↑ do not edit these entries | |
| ● Brief operative description | |
| Surgeon [M.D.] PGY Yr | Status ○SC ○SJ ○FA ○TA |
| Hospital / Service | Attending (F, L) |
| Program | First Assistant |
| History | |
| Preop Dx | |
| ● Postop Dx | |
| ● Operative findings | Pathology |
| Complication ○yes ○no | Complication Description /Management ● |
| Type of complication | Patient Followup |
| | Patient Outcome |

[ACS Data]  [More Data]

FIG. 4

| | | Search | Find All | Page Up |
|---|---|---|---|---|
| Click on a Procedure to Select It | | Clear | Cancel | Page Down |

| Section | Procedure |
|---|---|
| | SKIN |
| Skin and Soft Tissues | Major lymphadenectomy |
| Skin and Soft Tissues | Major excision for skin neoplasm |
| Skin and Soft Tissues | Radical excision of soft tissue tumor |
| Skin and Soft Tissues | Other major skin procedure |
| | HEAD AND NECK |
| Head and Neck | Lip resection |
| Head and Neck | Tongue resection |
| Head and Neck | Floor of mouth/buccal mucosa resect |
| Head and Neck | Parotidctomy |
| Head and Neck | Resect of other salivary glands |
| Head and Neck | Radical neck dissection |
| Head and Neck | Resection of mandible or maxilla |
| Head and Neck | Tracheostomy |
| Head and Neck | Other major head and neck |
| | BREAST |
| Breast | Breast biopsy |
| Breast | Simple mastectomy |
| Breast | Modified radical mastectomy |
| Breast | Radical mastectomy |
| Breast | Excis bx/quadrantect with ax dissect |
| Breast | Breast reconstruction |
| Breast | Other major breast surgury |
| | ALIMENTARY TRACT |
| Alimentary Tract | Esophagectomy |
| Alimentary Tract | Esophago-gastrectomy |
| Alimentary Tract | Antireflux procedure (open) |
| Alimentary Tract | Antireflux procedure (laparoscopic) |
| Alimentary Tract | Esophageal bypass procedure |
| Alimentary Tract | Repair of esophageal perforation |
| Alimentary Tract | Operations for esophageal stenosis |
| Alimentary Tract | Esophageal diverticulectomy |
| Alimentary Tract | Other major esophageal operations |
| Alimentary Tract | Gastrostomy (open) |
| Alimentary Tract | Gastrostomy (laparoscopic) |
| Alimentary Tract | Gastric resection; partial (open) |
| Alimentary Tract | Gastric resection; partial (lap) |
| Alimentary Tract | Gastric resection; total |
| Alimentary Tract | Vagot; trunc/select with drain (open) |
| Alimentary Tract | Vagot; trunc/select with drain (lap) |
| Alimentary Tract | Repair of gastric peforation |
| Alimentary Tract | Prox gastric vagot; high select (op) |
| Alimentary Tract | Prox gastric vagot; high select (lap) |
| Alimentary Tract | Gastroc reduct for morbid obesity |
| Alimentary Tract | Other major gastric cases |
| Alimentary Tract | Enterolysis |
| Alimentary Tract | Enterectomy (open) |
| Alimentary Tract | Enterectomy (laparoscopic) |
| Alimentary Tract | Repair of duodenal perforation |
| Alimentary Tract | Repair of jej/ileal perforation |
| Alimentary Tract | lieostomy (not with colectomy) |
| Alimentary Tract | Jej/ileal diverticulectomy |
| Alimentary Tract | Other major small bowel operation |
| Alimentary Tract | Appendectomy (open) |
| Alimentary Tract | Appendectomy (laparoscopic) |
| Alimentary Tract | Colostomy (all types) |
| Alimentary Tract | Colostomy closure |
| Alimentary Tract | Colostomy; partial (open) |
| Alimentary Tract | Cloostomy; partial (laparoscopic) |
| Alimentary Tract | Colect; tot or subtot w/ileost (open) |
| Alimentary Tract | Colect; tot or subtot w/ileost (lap) |

FIG. 5

Click on a numeric value to select a CPT code.
Click on a text field to see more text.

| System | Region | Category | Procedure | Code |
|---|---|---|---|---|
| Integumentary System | SKIN | EXCISION-DEBRIDE | Debridement; skin, subcutaneous tissue, and muscle | 11043 |

Search    Find All ← 620

Clear current CPT code    Cancel

FIG. 6B

Click on a numeric value to select a CPT code.
Click on a text field to see more text.

[Search] [Find All]

| System | Region | Category | Procedure | Code |
|---|---|---|---|---|
| Integumentary System | SKIN | INCISION AND | INCISION AND DRAINAGE | |
| Integumentary System | SKIN | INCISION AND | *Acne surgery (eg, marsupialization, opening or removal of | 10040 |
| Integumentary System | SKIN | INCISION AND | *Incision and drainage of abscess (eg, carbuncle, | 10060 |
| Integumentary System | SKIN | INCISION AND | Incision and drainage of abscess (eg, carbuncle, suppurative | 10061 |
| Integumentary System | SKIN | INCISION AND | *Incision and drainage of pilonidal cyst; simple | 10080 |
| Integumentary System | SKIN | INCISION AND | Incision and drainage of pilonidal cyst; complicated | 10081 |
| Integumentary System | SKIN | INCISION AND | *Incision and removal of foreign body, subcutaneous | 10120 |
| Integumentary System | SKIN | INCISION AND | Incision and removal of foreign body, subcutaneous tissues; | 10121 |
| Integumentary System | SKIN | INCISION AND | *Incision and drainage of hematoma, seroma or fluid | 10140 |
| Integumentary System | SKIN | INCISION AND | *Puncture aspiration of abscess, hematoma, bulla, or cyst | 10160 |
| Integumentary System | SKIN | INCISION AND | Incision and drainage, complex, postoperative wound | 10180 |
| Integumentary System | SKIN | EXCISION-DEBRIDE | EXCISION-DEBRIDEMENT | |
| Integumentary System | SKIN | EXCISION-DEBRIDE | *Debridement of extensive eczematous or infected skin; up | 11000 |
| Integumentary System | SKIN | EXCISION-DEBRIDE | Debridement of extensive eczematous or infected skin; each | 11001 |
| Integumentary System | SKIN | EXCISION-DEBRIDE | Debridement; skin, partial thickness | 11040 |
| Integumentary System | SKIN | EXCISION-DEBRIDE | Debridement; skin, full thickness | 11041 |
| Integumentary System | SKIN | EXCISION-DEBRIDE | Debridement; skin, and subcutaneous tissue skin | 11042 |
| Integumentary System | SKIN | EXCISION-DEBRIDE | Debridement; skin, subcutaneous tissue, and muscle | 11043 |
| Integumentary System | SKIN | EXCISION-DEBRIDE | Debridement; subcutaneous tissue, muscle, and bone | 11044 |
| Integumentary System | SKIN | PARING OR | PARING OR CURETTEMENT | |
| Integumentary System | SKIN | PARING OR | *Paring or curettement of benign hyperkeratotic skin lesion | 11050 |
| Integumentary System | SKIN | PARING OR | Paring or curettement of benign hyperkeratotic skin lesion | 11051 |
| Integumentary System | SKIN | PARING OR | Paring or curettement of benign hyperkeratotic skin lesion | 11052 |
| Integumentary System | SKIN | BIOPSY | BIOPSY | |
| Integumentary System | SKIN | BIOPSY | Biopsy of skin, subcutaneous tissue and/or mucous | 11100 |
| Integumentary System | SKIN | BIOPSY | Biopsy of skin, subcutaneous tissue and/or mucous | 11101 |
| Integumentary System | SKIN | REMOVAL OF SKIN | REMOVAL OF SKIN TAGS | |

[Clear current CPT code] [Cancel]

MEDICAL INFORMATION LOG SYSTEM

This application contains Microfiche Appendix consisting of one Slide and 74 Frames.

COPYRIGHT NOTICE

A portion of the disclosure of this patent document contains material which is subject to copyright protection. The copyright owner has no objection to the xeroxographic reproduction by anyone of the patent document or the patent disclosure in exactly the form it appears in the Patent and Trademark Office patent file or records, but otherwise reserves all copyright rights whatsoever.

BACKGROUND OF THE INVENTION

The present invention is directed to a medical information log system, and more particularly to advanced features in a surgical operative log system.

The ReSOLution package from Information Science Associates (ISA) is a DOS based program created specifically for the Accreditation Council for Graduate Medical Education (ACGME) and Residency Review Committee (RRC) for surgery. The program is not network compatible, is not cross-platform capable, and does not incorporate Current Procedural Terminology (CPT) menus or coding for forms for the American College of Surgeons (ACS). CPT is a standard numerical coding scheme. Its specific advantage is that it can download information directly to ACGME/RRC reporting diskettes which are the required method of reporting operative data by surgical residents and surgical training programs to the ACGME and RCC.

Summit from Summit Medical is a specific package for tracking pre, peri, and post operative variables, as well as outcomes for cardiothoracic surgery. While fairly comprehensive, its specific disadvantages are that it is expensive, not cross-platform capable, and does not address the specific needs of cardiothoracic residents. Specifically, it does not attempt to assist cardiothoracic surgery residents with completing required forms for the American Board of Thoracic Surgery certification (ABTS—the RRC equivalent for cardiothoracic surgery).

The TRACS package was designed specifically to track trauma and, to a less extent, critical care patients on surgical services. This package does not do coding for the RRC or the ACS, and does not cover any areas of General Surgery other than trauma, let alone other surgical specialties.

Surgical Procedure Log™ (SPL) from Medical Software Solutions, Inc. is a member of the FileMaker Database market. Databases were created in FileMaker Pro, and these databases were applied to multiple specialties. FileMaker has major problems when dealing with large databases. For example, the current FileMaker version does not support files larger than 32 MByte (about 32K operations). In addition, SPL does not incorporate ACS coding forms.

The package from the American College of Surgeons (ACS) includes a program written in FoxPro (Windows version only) limited to general cancer database (outcomes package). This is not an operative log, and it does not generate RRC, ACS, or similar reports.

VascuBase for Vascular Surgeons from Consensus Medical Systems, Inc. is a surgical log and outcomes package for vascular surgeons only. This package includes statistics and some graphics, but it does not generate report forms for residents for the RRC. Thus, this package is limited by specialty and directed at practicing surgeons, but not surgeons in training (residents).

Most surgical log systems are for full departments only. Thus, a system for either a full department or individual use is needed. Additionally, a system which functions across multiple specialties is desirable.

SUMMARY OF THE INVENTION

In the preferred embodiment, the present invention utilizes a computer system to provide a medical information log system. A mouse and/or a keyboard is used to input data for various medical log entries. These log entries are associated with a medical visit, and they contain information related to the doctor and the type of said medical visit. Each medical visit has only one log entry associated with it. The inputted data is stored within an organized database located in the computer's memory. The computer's controller is used to track the inputted data for various information. This information includes record keeping, outcome analysis, research, teaching, quality assurance, and/or billing. The inputted data is displayed when desired.

These and other advantages will become apparent to those skilled in this art upon a reading of the following detailed description of the invention, which should be taken in conjunction with the accompanying drawings.

BRIEF DESCRIPTION OF THE DRAWINGS

FIG. 4 is an example of a screen display provided by the computer application for data entry;

FIG. 5 is an example of groupings of RRC procedure codes used in screen displays for data entry;

FIGS. 6A–C are examples of screen displays for finding a CPT code from a list during data entry;

FIG. 8 is an example of the main data entry screen display;

FIG. 9A is an example of a screen display for entering more diagnoses;

FIG. 14 is an example of a screen display of a case summary report by date.

DESCRIPTION OF PREFERRED EMBODIMENTS

The present invention can be used for either a full department or individual use. In addition, the present invention provides a single package which: 1) functions across multiple specialties; and 2) can be modified to accommodate an additional specialty. The present computer application system can hold an extremely large number of operation records. Additionally, reports related to these operation records can be quickly generated.

Figure 1:
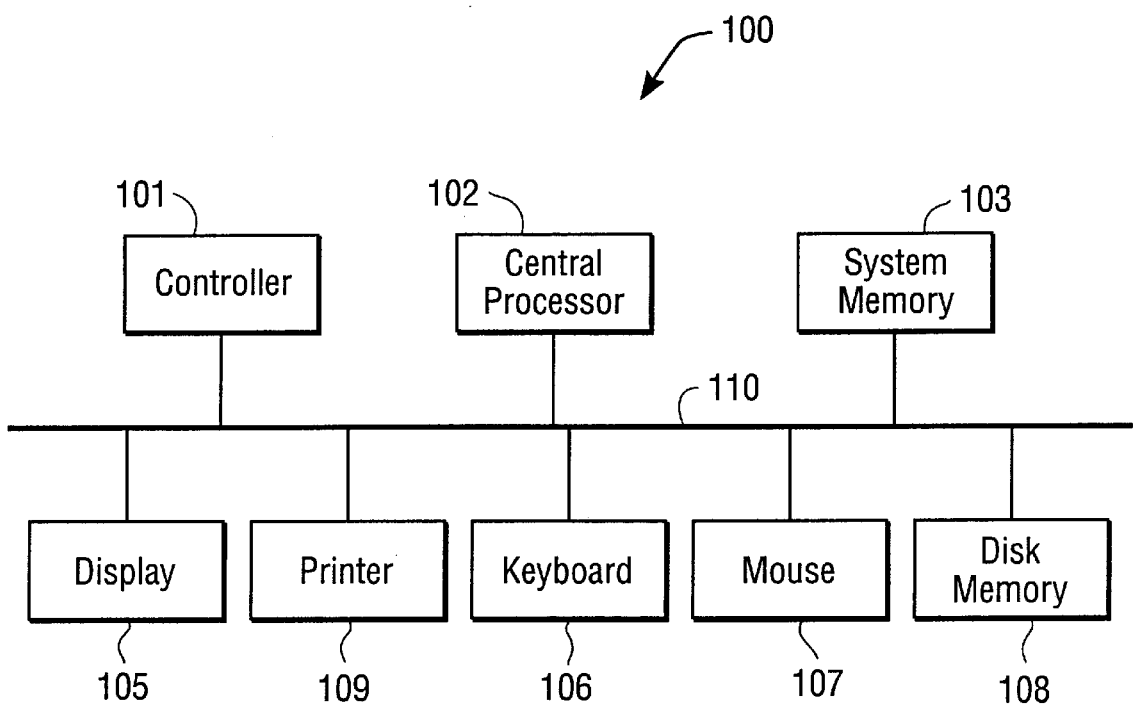
FIG. 1 is a block diagram of a computer system in which the invention may be embodied.

FIG. 1 is a block diagram of a computer system in which the invention may be embodied. The preferred embodiment of the invention is implemented on a computer system 100 having a processor 102, a system memory 103, a display device 105, a keyboard 106, a mouse 107, a disk memory 108, an I/O controller 101, a printer 109, and an interconnecting device 110, such as a system bus. Disk memory 108 may consist of hard disk(s), floppy disk(s), CD-ROM(s), PCMCIA or other plug-in memory device(s), and the like.

Figure 2:
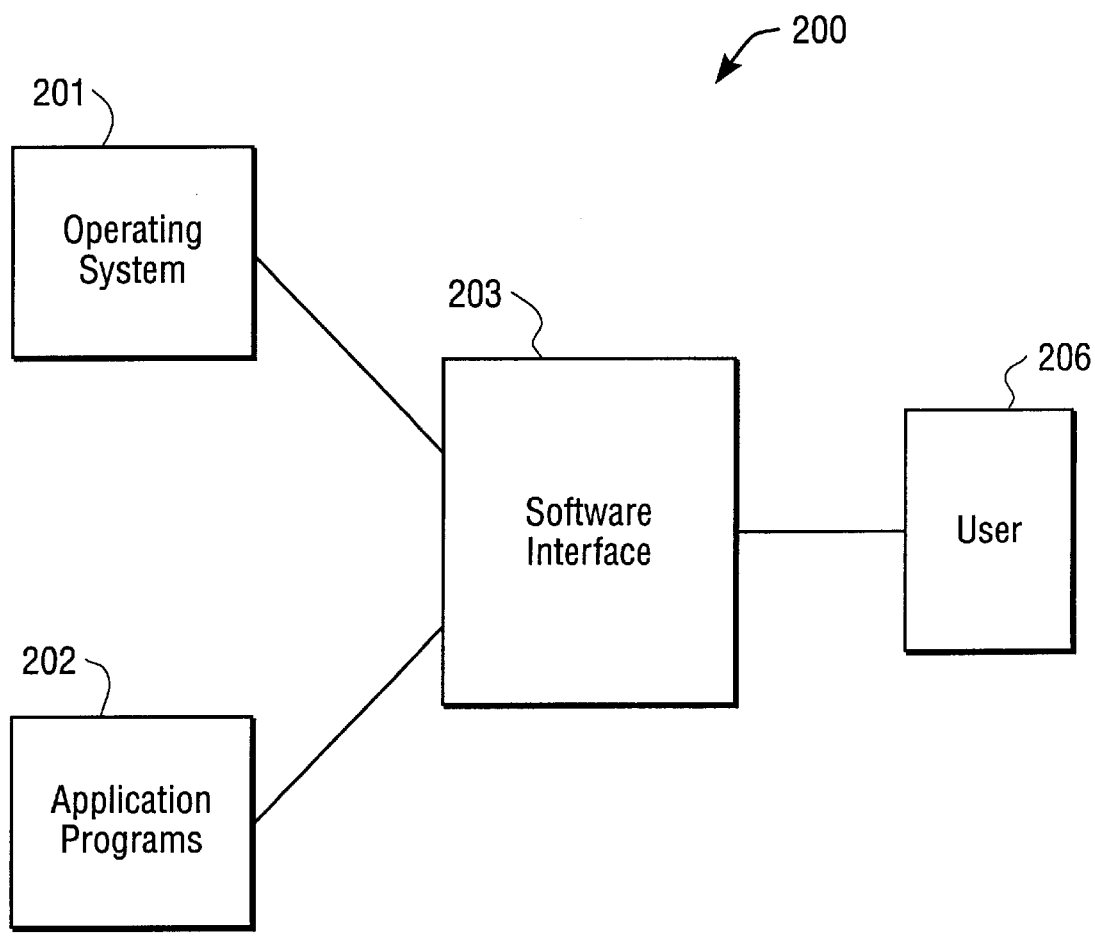
FIG. 2 is a block diagram of a computer software system used in the preferred embodiment.

FIG. 2 is a block diagram of a computer software system used in the preferred embodiment. A computer software system 200 is used to program the computer system of FIG. 1. Software system 200 is stored in system memory 103 and on disk memory 108. Software system 200 programs the central processor 102 to display a graphic user interface (GUI) on display monitor 105. In the preferred embodiment, software interface 203 provides an interface between a user 206, an operating system 201, and a computer application 202. It will be apparent that one of ordinary skill in the art, informed by this application, could implement the invention in other operating environments.

In the preferred embodiment, computer application 202 is a surgical operative log system written to use the FoxPro database engine. This operative log system can also be written to use the Filemaker database engine, and the like. Computer application 202 is compatible with DOS, UNIX, Mac and Windows systems. While a surgical operative log system is provided in the preferred embodiment, the present invention also provides a log system for any type of medical information including medical visits, minor medical procedures, and medical operations.

Figure 3:
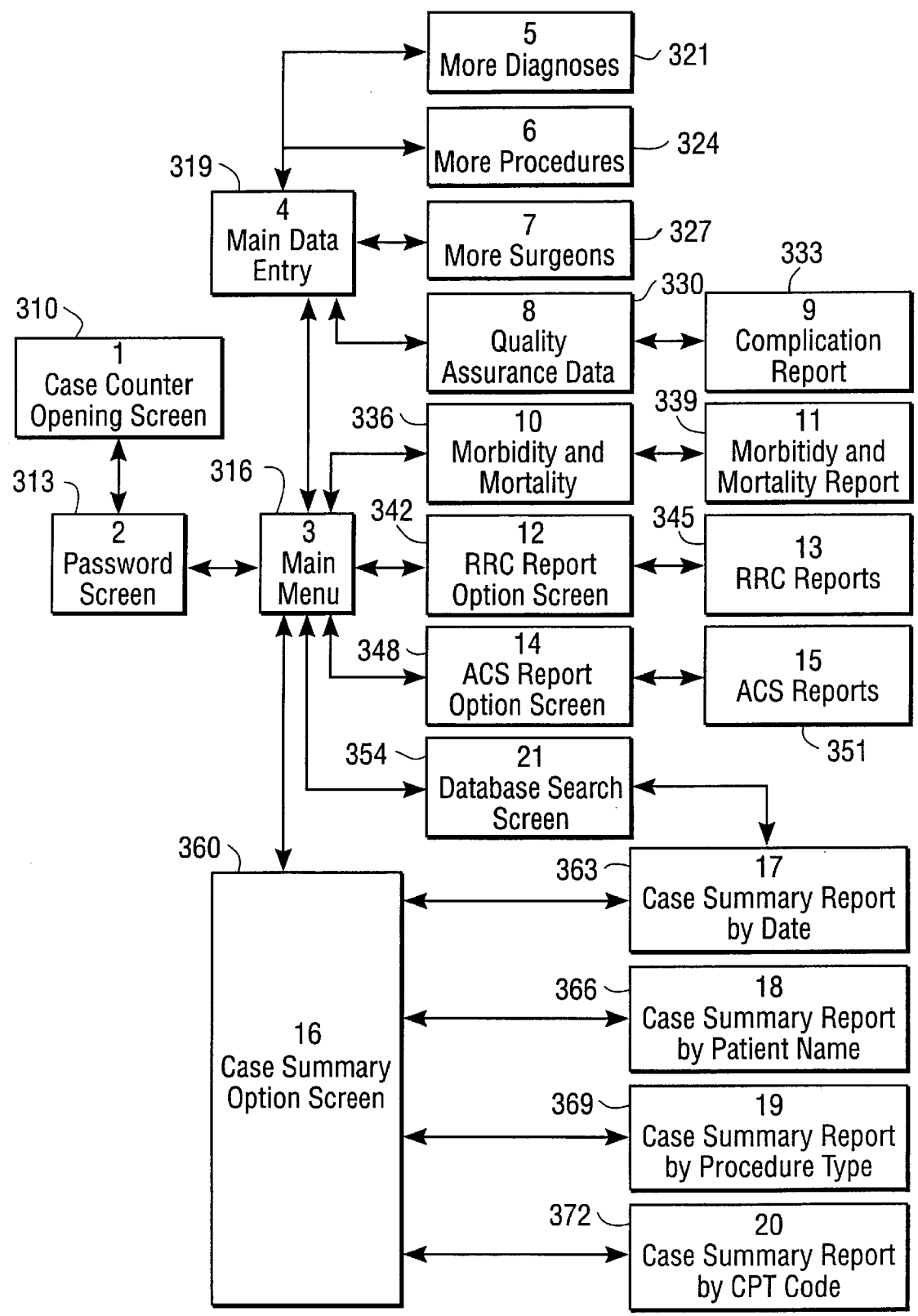
FIG. 3 is a process flowchart for the various functions provided by the computer application.

FIG. 3 is a process flowchart for the various functions provided by the computer application. In the preferred embodiment, there is a correspondence between functions and screens displayed on display device 105, but it is understood that the functions may be organized and implemented in other ways, even without the use of screens. For example, information requesting prompts could be provided to the user on a printer.

When a user begins operative log computer application 202, the first screen displayed on display device 105 is Case Counter Opening Screen 310. From Case Counter Opening Screen 310, The user can choose to proceed to Password Screen 313. At Password Screen 313, if the user types the correct password in response to a prompt, he can proceed to Main Menu 316.

From Main Menu 316, the user can choose to proceed to Main Data Entry Screen 319. At Main Data Entry Screen 319, the user can enter data for operation(s). This data can include, for each operation, the following: Patient First Name, Patient Middle Name, Patient Last Name, Patient Initials, Patient Date of Birth, Patient Age, Patient Medical Record Number, Patient Sex, Date of operation, Outpatient Arrival Indicator, Operative Note Dictated Indicator, Inpatient Indicator, Brief Operative Description, CPT Code, CPT Text Description, RRC Category, RRC CPT Code, RRC Procedure Description, RRC Pediatric/Trauma Indicator, Surgical Program Name, surgeon Name, Surgeon Post Graduate Year, Surgeon Status, Hospital, Surgical Service, Attending Surgeon First Name, Attending Surgeon Last Name, Patient History, Patient Pre operative Diagnosis, Patient Post Operative Diagnosis, Operative Findings, Pathology, Complication Indicator, Patient Outcome, and Patient Followup. A CPT (Current Procedural Terminology) Code, from this paragraph above, is one procedure from a detailed standard list of procedures. An RRC (Residency Review Committee) Procedure Description, from this paragraph above, is one procedure from the RRC's less-detailed, standard list of procedures. Because the RRC's list of procedures is shorter than the CPT list, certain procedures which would be classified differently in the CPT scheme would be classified as the same under the RRC scheme. The RRC has provided a default one-to-one mapping from each of its procedures into a "corresponding" CPT procedure. This mapping is adequate for many purposes, but for a particular procedure which has been classified into an RRC procedure, the default mapping may not supply the best CPT Code for that procedure. The RRC CPT Code, from this paragraph above, is a datum kept by the computer application to remedy the deficiencies of the RRC mapping. The RRC CPT Code is a CPT Code which the user may enter for an actual procedure, which will override the RRC's default mapping in those places where the RRC's default mapping would otherwise be used, for example, in generating certain reports. An RRC Category is a broad characterization of procedures according to a list of categories chosen by the RRC. In the preferred embodiment, the present invention is used for operations performed by surgeons. The present invention can also be used for any type medical visit involving any type of doctor.

From Main Data Entry Screen 319, the user can choose to proceed to More Diagnoses Screen 321. At More Diagnoses Screen 321, the user can enter diagnoses (e.g., six diagnoses can be entered at one time). For each diagnosis, the user can enter Diagnosis Number, Pre Operative Diagnosis, Post Operative Diagnosis, and ICD9 Code. An ICD9 Code conforms to the International Classification of Disease, 9th Revision. From More Diagnoses Screen 321, the user can return to Main Data Entry Screen 319 or, as a shortcut, proceed directly to More Procedures Screen 324.

From Main Data Entry Screen 319, the user can choose to proceed to More Procedures Screen 324. At More Procedures Screen 324, the user can enter multiple procedures (e.g., six procedures at one time). For each procedure, the user can enter Procedure Number, RRC Procedure Category, RRC Procedure Classification, RRC Procedure Type, RRC CPT Code, Procedure Note, and CPT Code. The RRC Procedure Type is another very broad classification of Procedures defined by the RRC. From More Procedures Screen 324, the user can return to Main Data Entry Screen 319, or as a shortcut, proceed directly to More Diagnoses Screen 321.

From Main Data Entry Screen 319, the user can choose to proceed to More Surgeons Screen 327. At More Surgeons Screen 327, the user can enter surgeons. Data which can be entered at Main Data Entry Screen 319 include Principal Surgeon Name, Additional Surgeon Names (e.g., four additional names may be entered), Procedure Note (e.g., six notes may be added), RRC Coding Matrix (e.g., five Total Surgeons by six Procedures may be entered). From More Surgeons Screen 327, the user can return to Main Data Entry Screen 319.

From Main Data Entry Screen 319, the user can choose to proceed to Quality Assurance Data Screen 330. At Quality Assurance Data Screen 330, the user can enter data related to complication(s), including Type of Complication (e.g., four types may be entered), and Complication Description and Management. The user can also cause to be generated Complication Report 333, which contains data from multiple sources, including those entered in Quality Assurance Data Screen 330 and other screens. The information provided by Complication Report 333 is of the type frequently needed for reports required by hospitals or other organizations. Complication Report 333 may be displayed on display device 105, stored as a file in disk memory 108, or printed by printer 109. From Quality Assurance Data Screen 330, the user can return to Main Data Entry Screen 319.

From Main Data Entry Screen 319, the user can choose to return to Main Menu 316. From Main Menu 316, the user can choose to proceed to Morbidity and Mortality Screen 336. From Morbidity and Mortality Screen 336, the user can cause to be generated Morbidity and Mortality Report 339, which contains statistics related to morbidity and mortality. The information provided by this report is of the type frequently needed for reports required by hospitals or other organizations. The user specifies the set of data for computing statistics by entering restrictions such as Beginning and Ending Dates, Hospital(s), and Surgical Services. Morbidity and Mortality Report 339 may be displayed on display device 105, stored as a file in disk memory 108, or printed by printer 109. From Morbidity and Mortality Screen 336, the user can return to Main Menu 316.

From Main Menu 316, the user can choose to proceed to RRC Report Option Screen 342. From RRC Report Option Screen 342, the user can cause to be generated RRC Report (s) 345, which contain all data required for reporting to the RRC and are of the required layout. These report(s) also contain all data required for reporting to the ABS (American Board of Surgery). The user specifies the type(s) of RRC Report(s) 345 to generate, including those for Major Cases, Minor Cases, Other Major Cases, or Laparoscopic Cases. The user may specify that RRC Report(s) 345 be generated as Hybrid Report(s) With RRC And CPT Codes. Hybrid Reports are based on the RRC layout, but include additional information, including CPT Codes. RRC Report(s) 345 may be displayed on display device 105, stored as a file in disk memory 108, or printed by printer 109. From RRC Report Option Screen 342, the user can return to Main Menu 316.

From Main Menu 316, the user can choose to proceed to ACS Report Option Screen 348. From ACS Report Option Screen 348, the user can cause to be generated ACS Report (s) 351, which contain statistics required for reporting to ACS (American College of Surgeons), including those which make use of ACS's classification scheme for procedures. The user specifies the types of statistics to be included in ACS Report(s) 351, including those for Inpatients or Outpatient Arrivals. RRC Report(s) 345 may be displayed on display device 105, stored as a file in disk memory 108, or printed by printer 109. From ACS Report Option Screen 348, the user can return to Main Menu 316.

From Main Menu 316, the user can choose to proceed to Case Summary Option Screen 360. From Case Summary Option Screen 360, the user can cause to be printed Case Summary Report by Date 363, Case Summary Report by Patient Name 366, Case Summary Report by Procedure Type 369, or Case Summary Report by CPT Code 372. These case summary reports contain summary statistics for each case. The reports differ in the criterion by which cases are sorted into order. The user specifies which type(s) of Case Summary Report is to be printed. These case summary report(s) may be displayed on display device 105, stored as a file in disk memory 108, or printed by printer 109. From Case Summary Option Screen 360, the user can return to Main Menu 316.

From Main Menu 316, the user can choose to proceed to Database Search Screen 354. At this screen, the user can use a multiplicity of selection criteria to specify the cases for which summaries should be produced. The Case Summary Report by Date 363 that is produced has been described above. From Database Search Screen 354, the user can return to Main Menu 316.

FIG. 4 is an example of a screen display provided by the computer application for data entry. A screen such as screen display 400 is to be displayed on display device 105 by Main Data Entry Screen 319 as an electronic form whose fields may be filled in or modified by the user 206. To prevent accidental modifications and nonsensical entries, the software application allows certain fields, such as Surgeon Name, to be specially designated so that the software application will not permit the user to change those fields once they have been entered.

FIG. 5 is an example of groupings of RRC procedure codes used in screen displays for choosing an RRC procedure code during data entry. The user can cause a screen such as screen display 500 to be displayed on display device 105 by Main Data Entry Screen 319, More Procedures Screen 324, or another screen from which RRC codes may be entered by the user. The computer application provides such screens to permit the user to quickly choose the needed RRC procedure code without having to scroll through the entire list of codes. Instead, the computer application: 1) groups procedures according to sections, such as "head and neck"; 2) permits the user to specify the section to which the procedure belongs, by choosing from the small list of all sections; then 3) displays immediately the portion of the list containing RRC codes for procedures belonging to that section; and 4) permits the user to select one of the RRC codes displayed. If the user does not know the section, the computer application will permit the default mode of scrolling through the entire list of procedures.

Figure 6A:
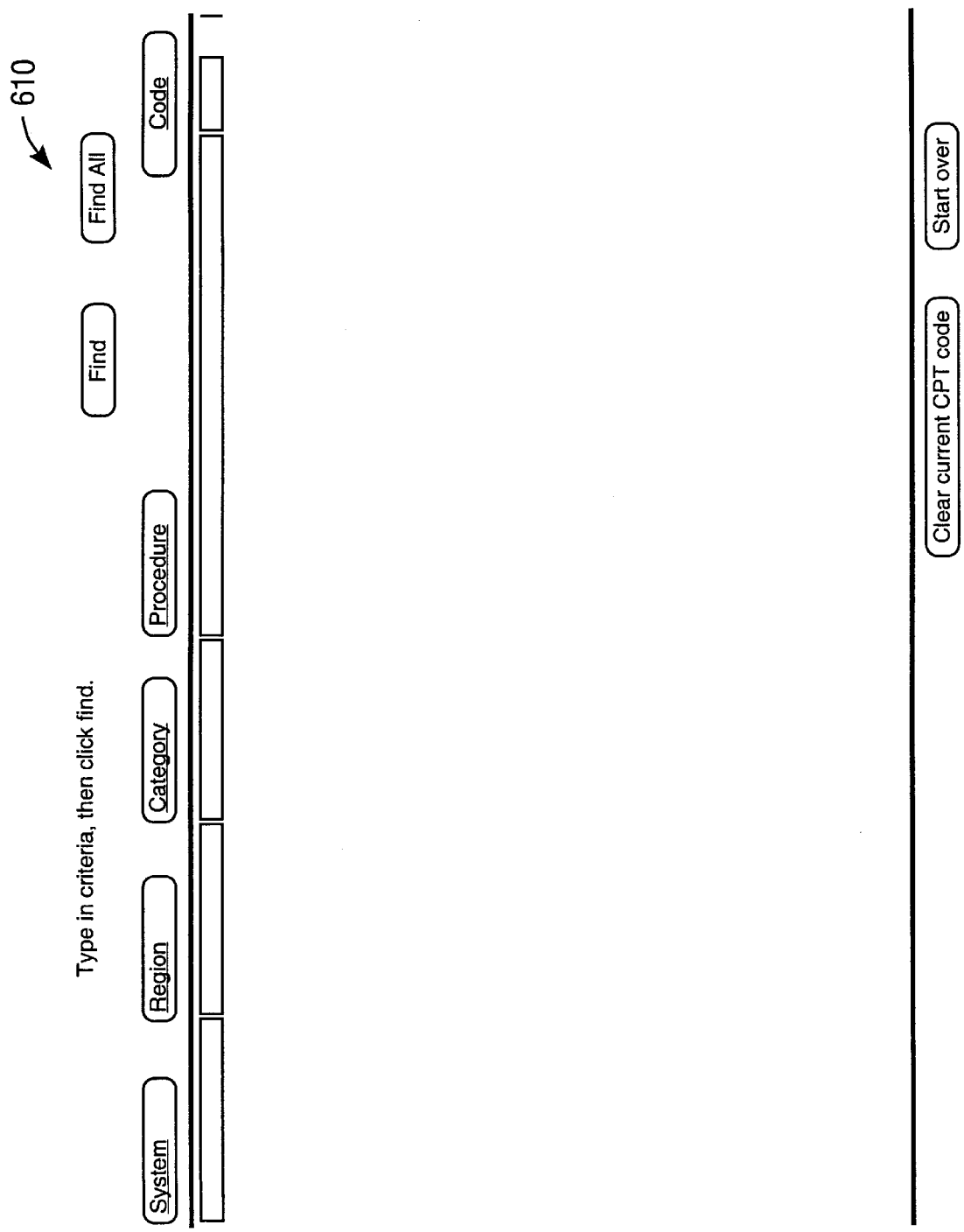

FIGS. 6A–C are examples of screen displays for finding a CPT procedure code during data entry. In the preferred embodiment, screens such as those in FIGS. 6A–C are displayed on display device 105 by Main Data Entry Screen 319, More Procedures Screen 324, or another screen from which CPT codes may be entered by the user. The computer application provides such screens to permit the user to quickly find the needed CPT procedure code from a large list. The user is not forced to scroll through the entire list of thousands of CPT codes. Instead, the computer application uses the AMA's (American Medical Association's) classification of CPT procedure codes according to four variables: system, region, category, and procedure. The user can specify those variables of the needed CPT code that the user knows, by choosing from small lists of all systems, all regions, all categories, and all procedures. Thereafter, the computer application will display the list of matching CPT procedure codes, from which the user can pick the desired one. Screen 610 in FIG. 6A is an example of a screen from which the user can specify the known variables of the needed CPT code. In addition to specifying known variables, the user can also enter directly to Screen 610 a CPT procedure code or a range of CPT procedure codes. Thereafter, the computer application will display the list of matching CPT procedure code(s) and their variables, from which the user can pick the desired one, or confirm that the one he picked was correct now that he sees its informative variables. Screen 620 in FIG. 6B is an example of a screen in which the user has specified directly a CPT procedure code and caused the computer application to display that procedure's informative variables so that the user can confirm it. Screen 630 in FIG. 6C is an example of a screen in which the user has specified directly a range of CPT procedure codes and caused the computer application to display CPT procedure codes within that range so that the user may choose one.

Figure 7:
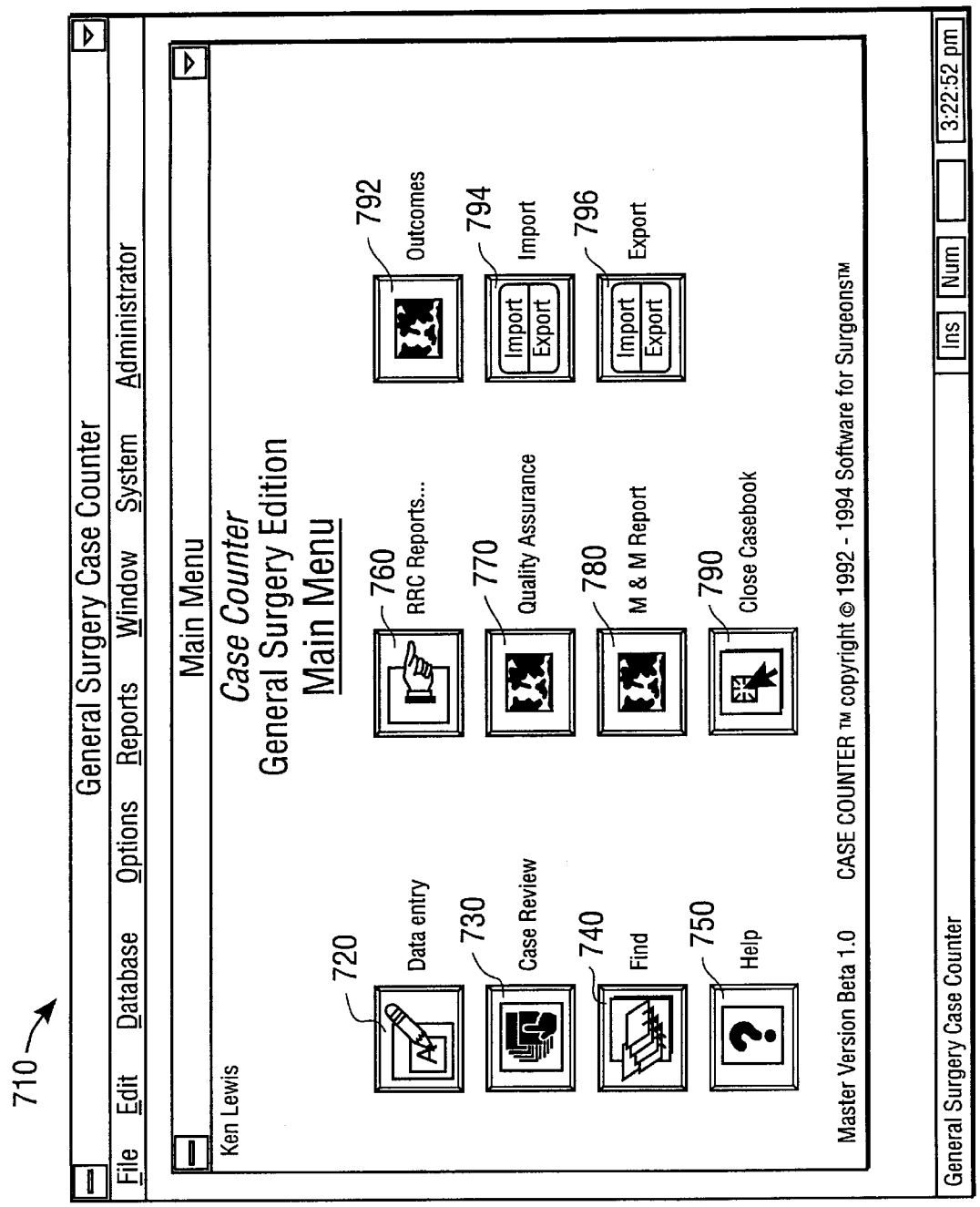
FIG. 7 is an example of the main menu screen display.
Figure 8:
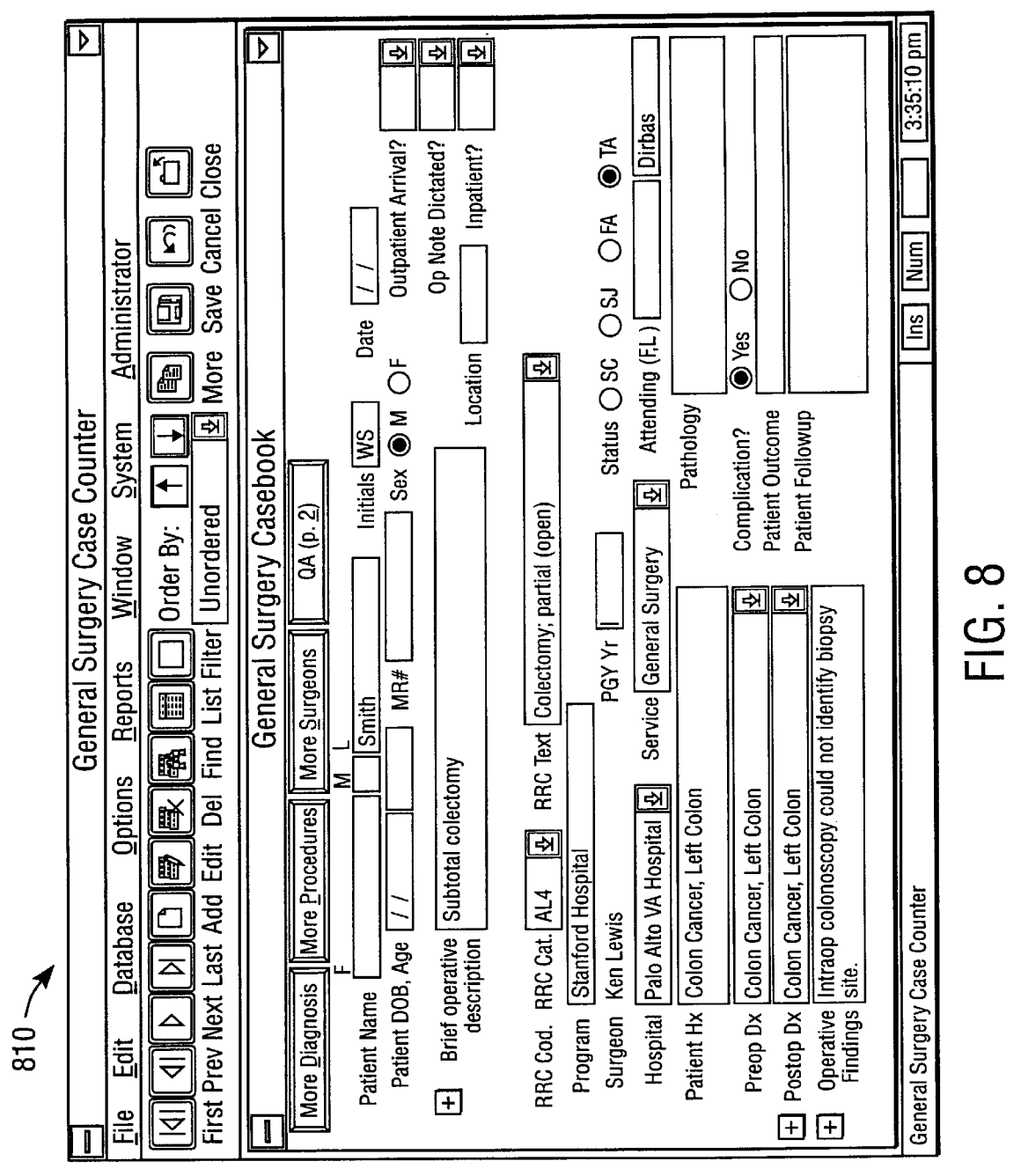

FIG. 7 is an example of the main menu screen display, which is Main Menu Screen 316 in FIG. 3. In the preferred embodiment, main menu screen display 710 is a standard Window display which includes icons for Data Entry 720, Case Review 730, Find 740, Help 750, RRC Reports 760, Quality Assurance 770, M&M Report 780, Close Casebook 790, Outcomes 792, Import 794, and Export 796. FIG. 8 is an example of the main data entry screen display, which is Main Data Entry Screen 319 in FIG. 3. As described above, various data related to a medical visit/procedure is entered via main data entry screen 810.

Figure 9A:
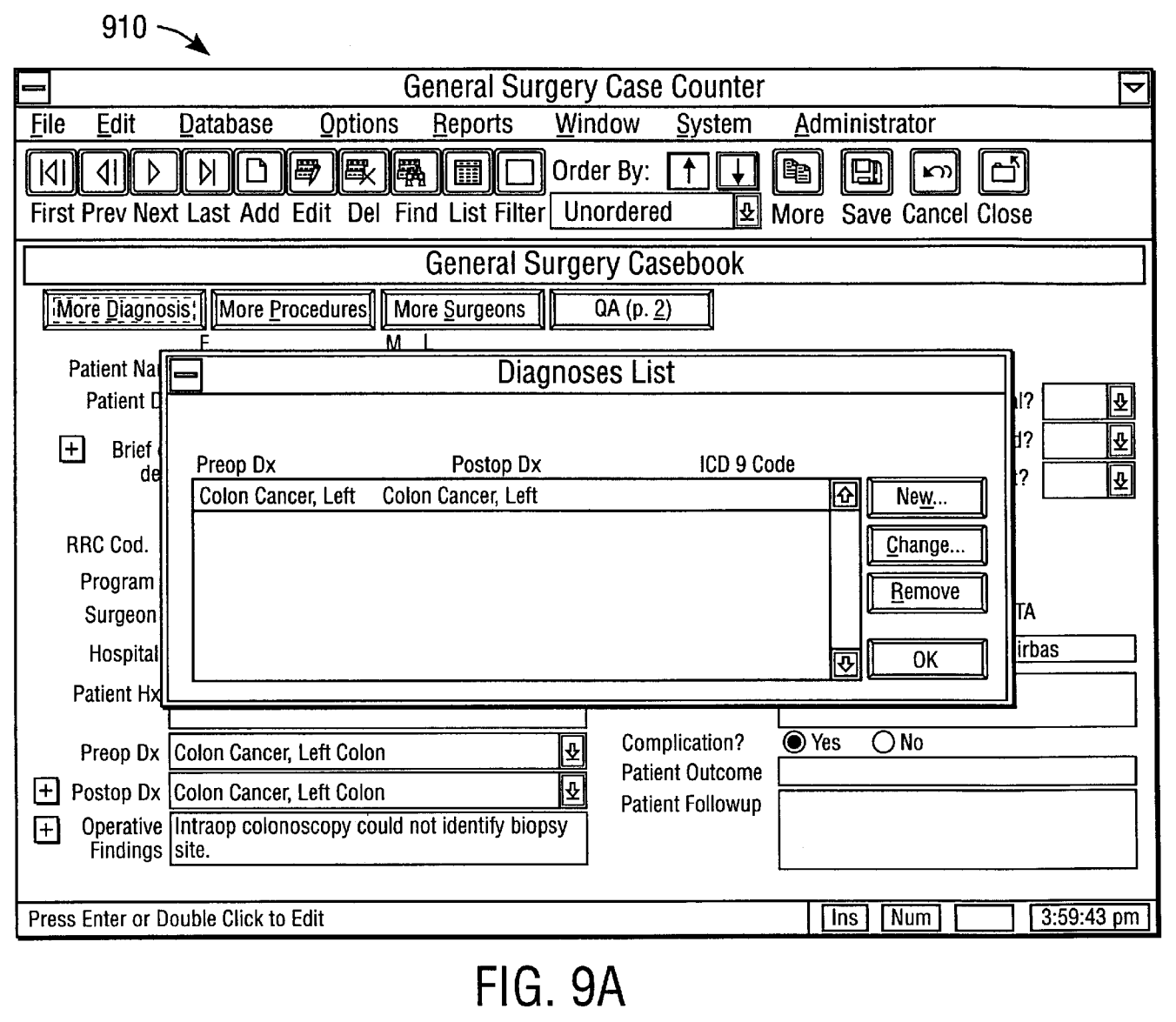
Figure 9B:
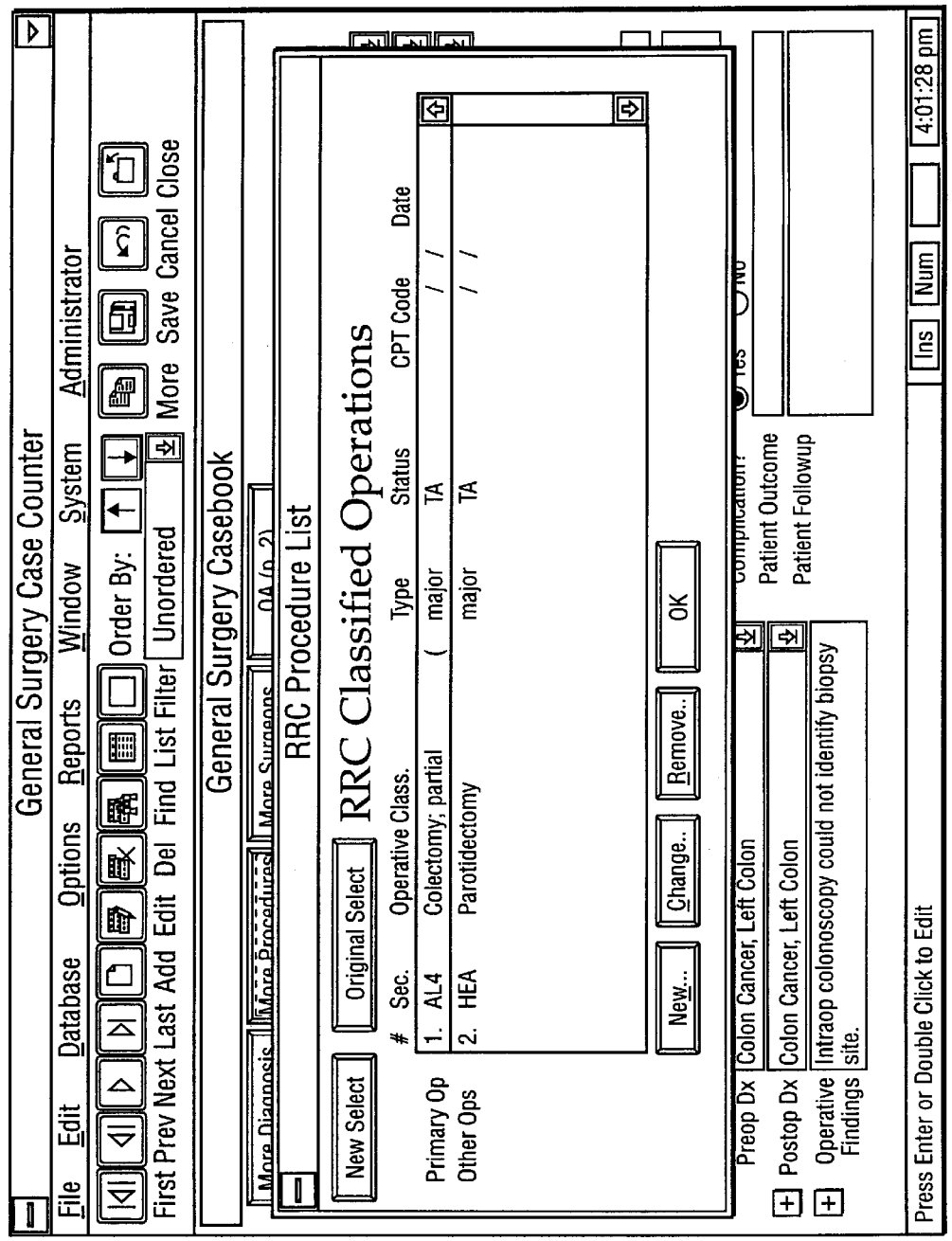
FIG. 9B is an example of a screen display for entering more procedures.

FIG. 9A is an example of a screen display for entering more diagnoses, which is More Diagnoses Screen 321 in FIG. 3. In the preferred embodiment, this screen display 910 is an overlay on the main data entry screen as shown in FIG. 9A. FIG. 9B is an example of a screen display for entering more procedures, which is More Procedures Screen 324 in FIG. 3. In the preferred embodiment, this screen display 920 is also an overlay on the main data entry screen as shown in FIG. 9B.

Figure 10:
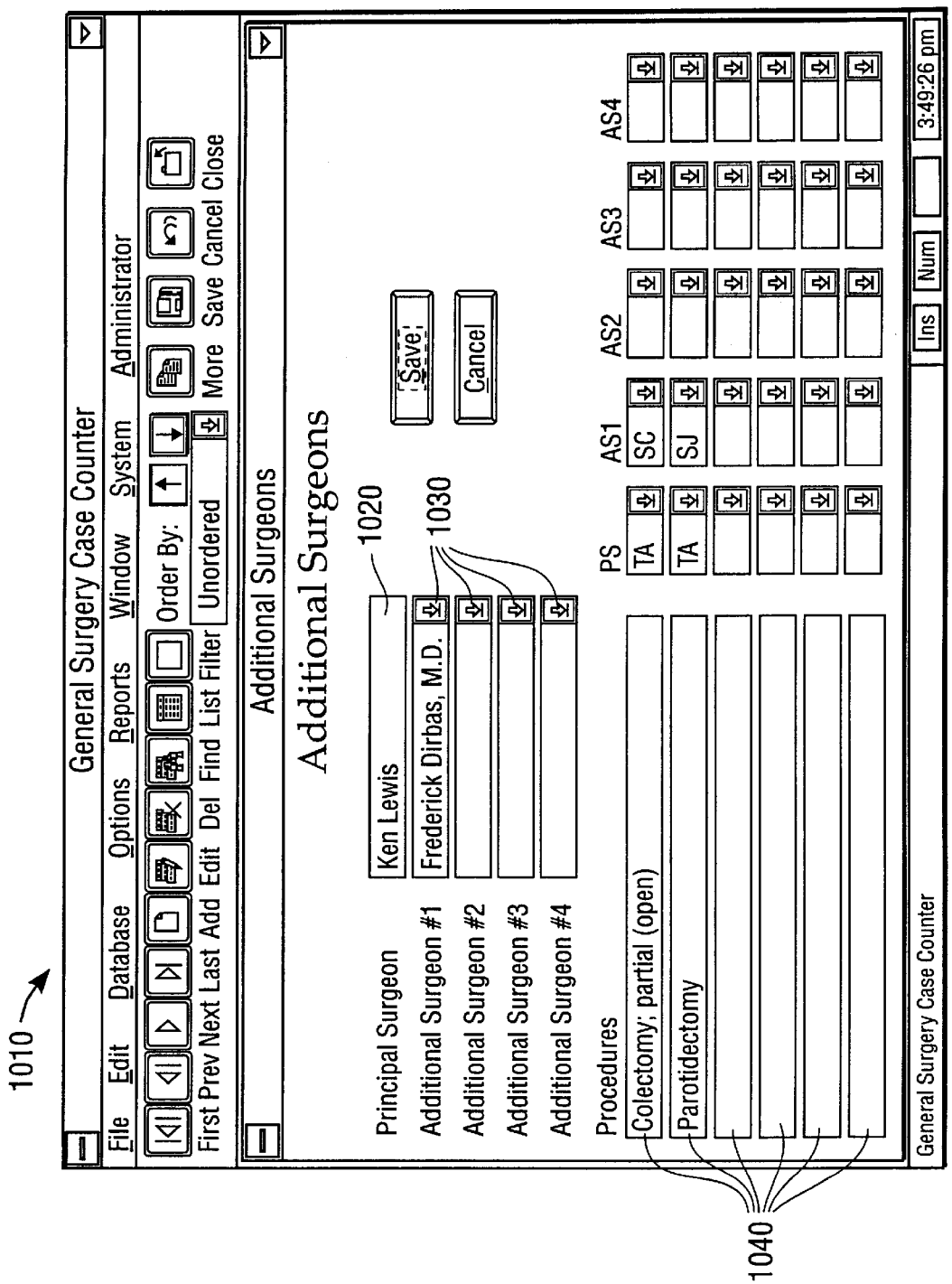
FIG. 10 is an example of a screen display for entering more surgeons.

FIG. 10 is an example of a screen display for entering more surgeons, which is More Surgeons Screen 327 in FIG. 3. In the preferred embodiment, this screen display 1010 has data entry spaces for a principal surgeon 1020, additional surgeons 1030, multiple procedures 1040, etc.

Figure 11A:
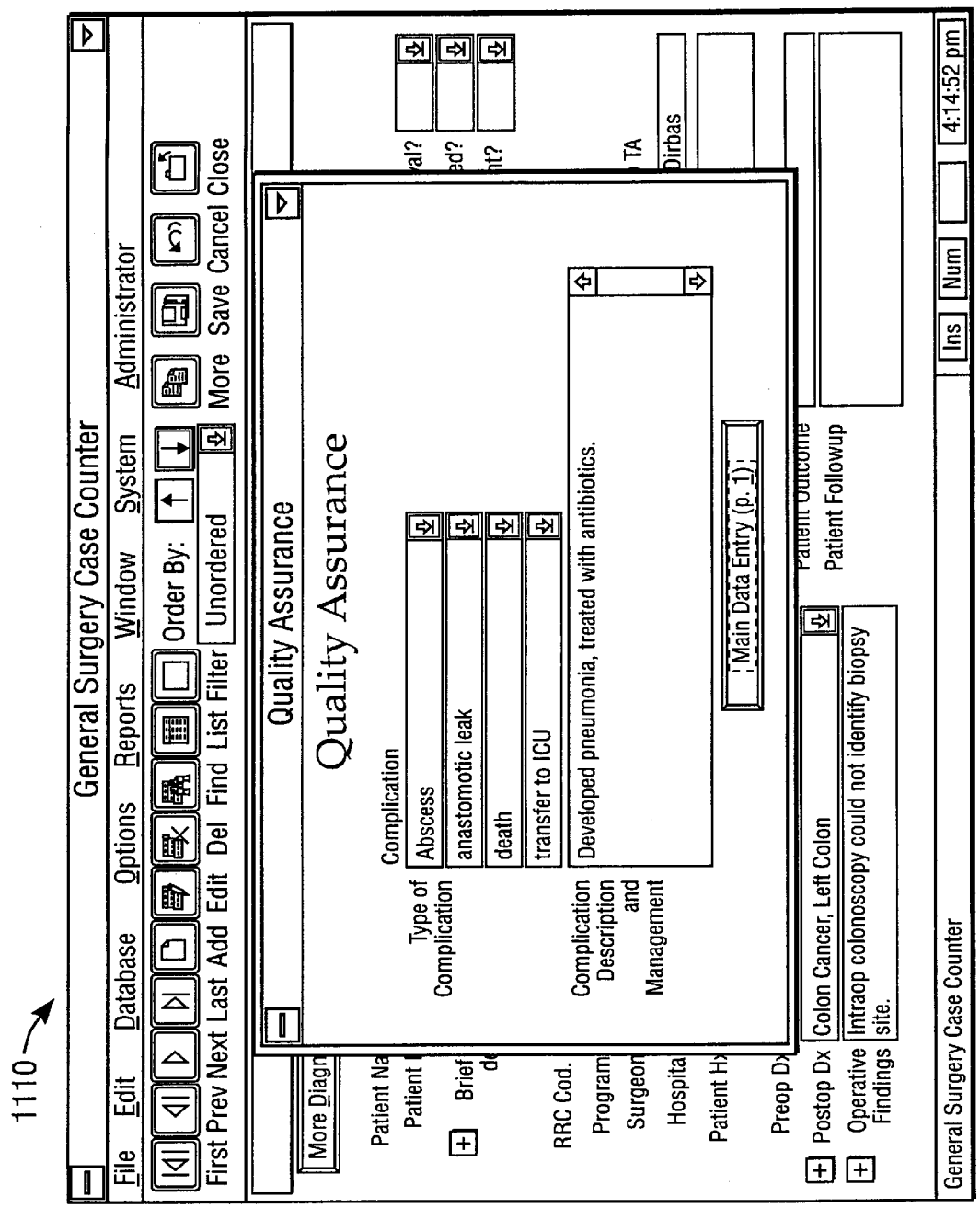
FIG. 11A is an example of a screen display for entering quality assurance data.
Figure 11B:
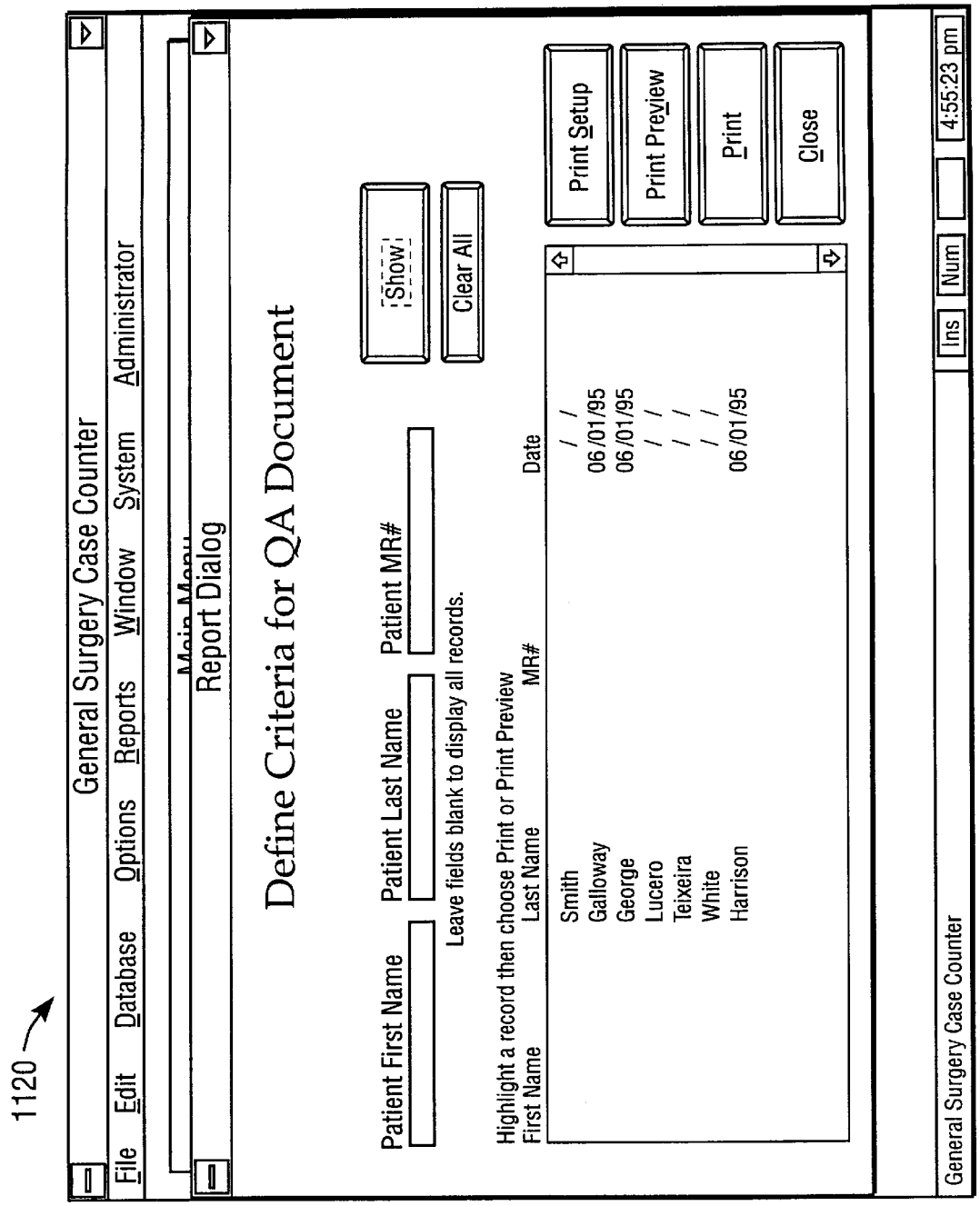
FIG. 11B is an example of a screen display for selecting the data to include in a complication report.

FIG. 11A is an example of a screen display for entering quality assurance data, which is More Procedures Screen 324 in FIG. 3. This screen display 1110 can contain complication information. FIG. 11B is an example of a screen display 1120 for selecting the data to include in a complication report, which is Quality Assurance Data Screen 330 in FIG. 3.

Figure 12:
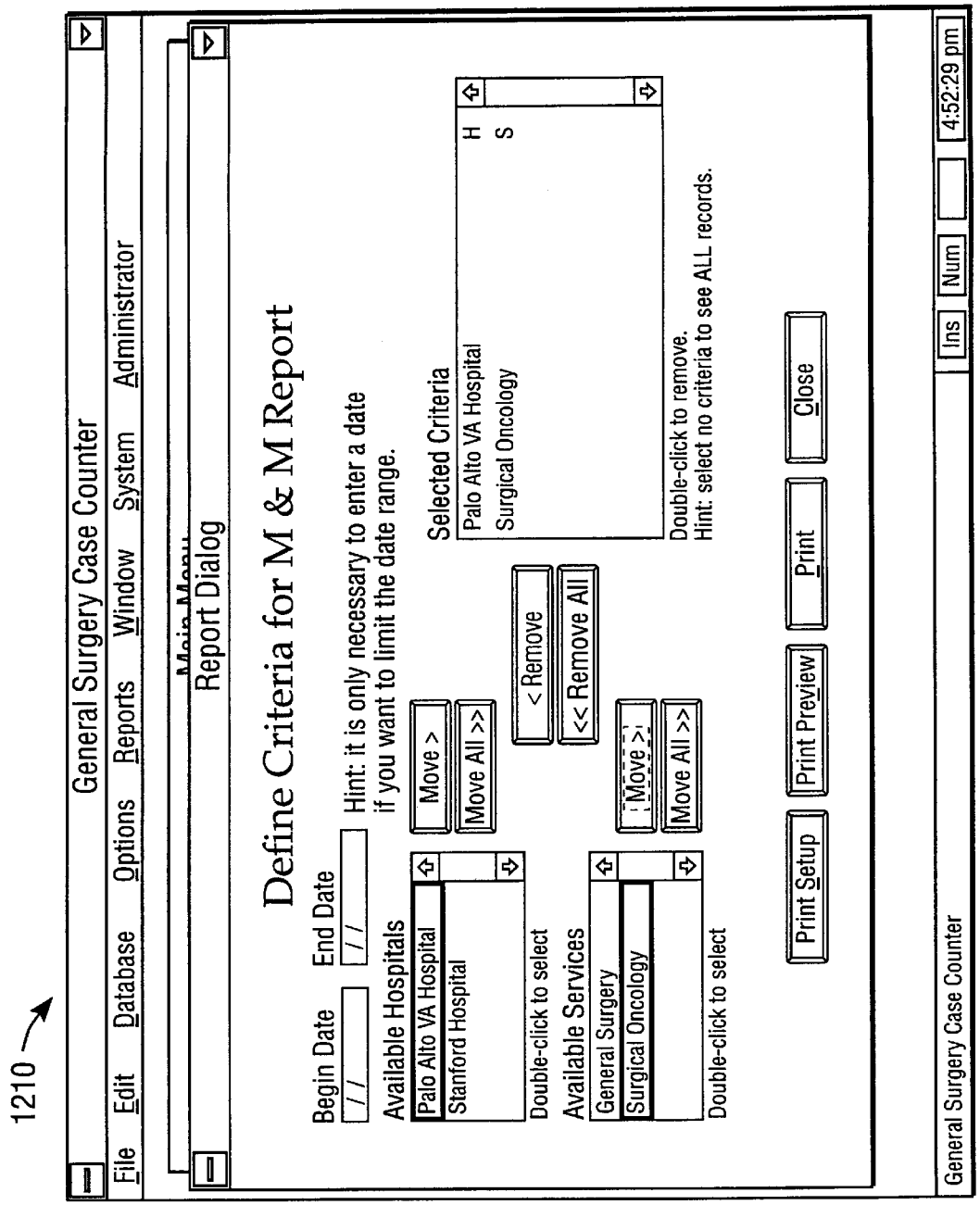
FIG. 12 is an example of a screen display for selecting the data to include in a morbidity and mortality report.
Figure 13:
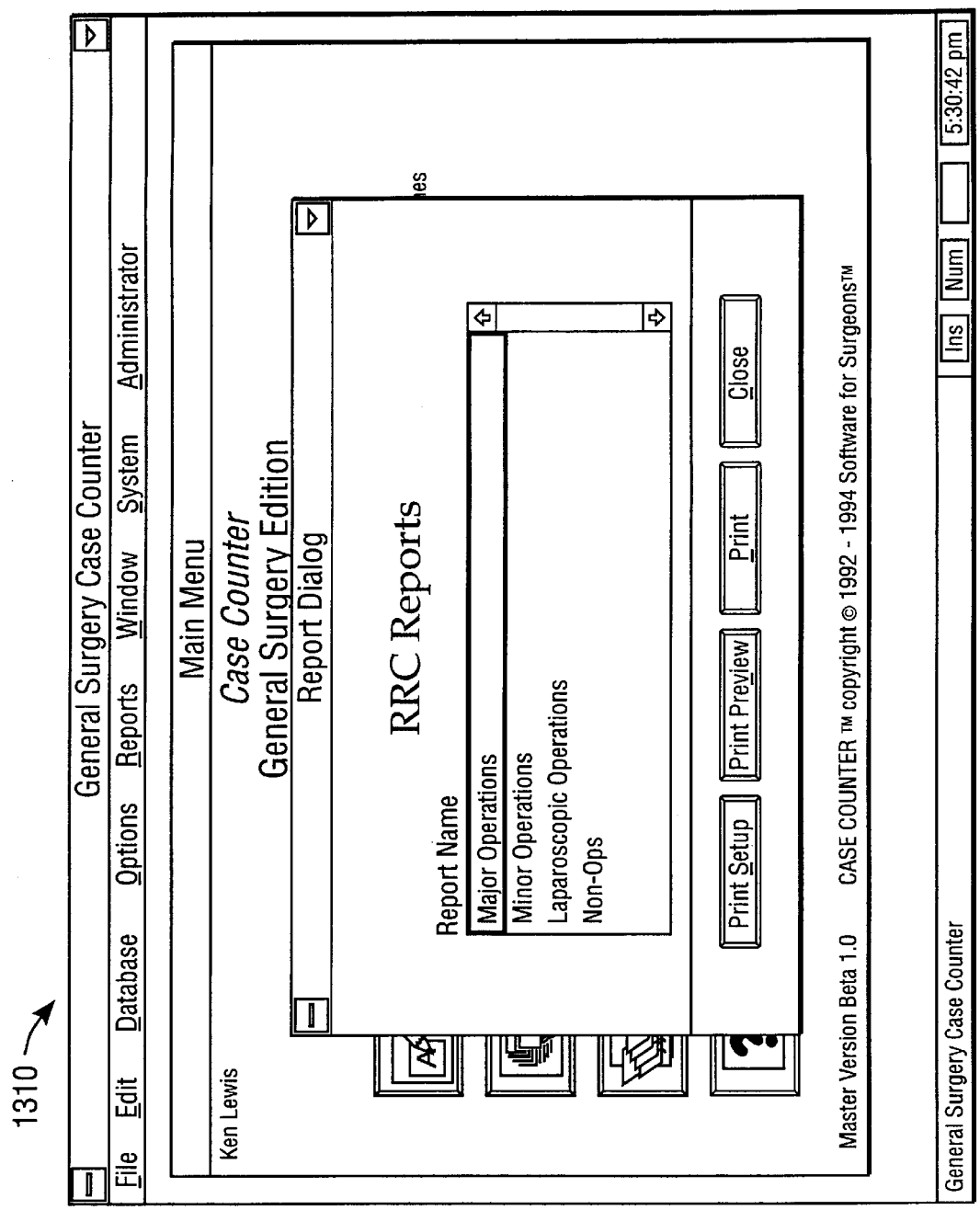
FIG. 13 is an example of a screen display for selecting the data to include in an RRC report.
Figure 14:
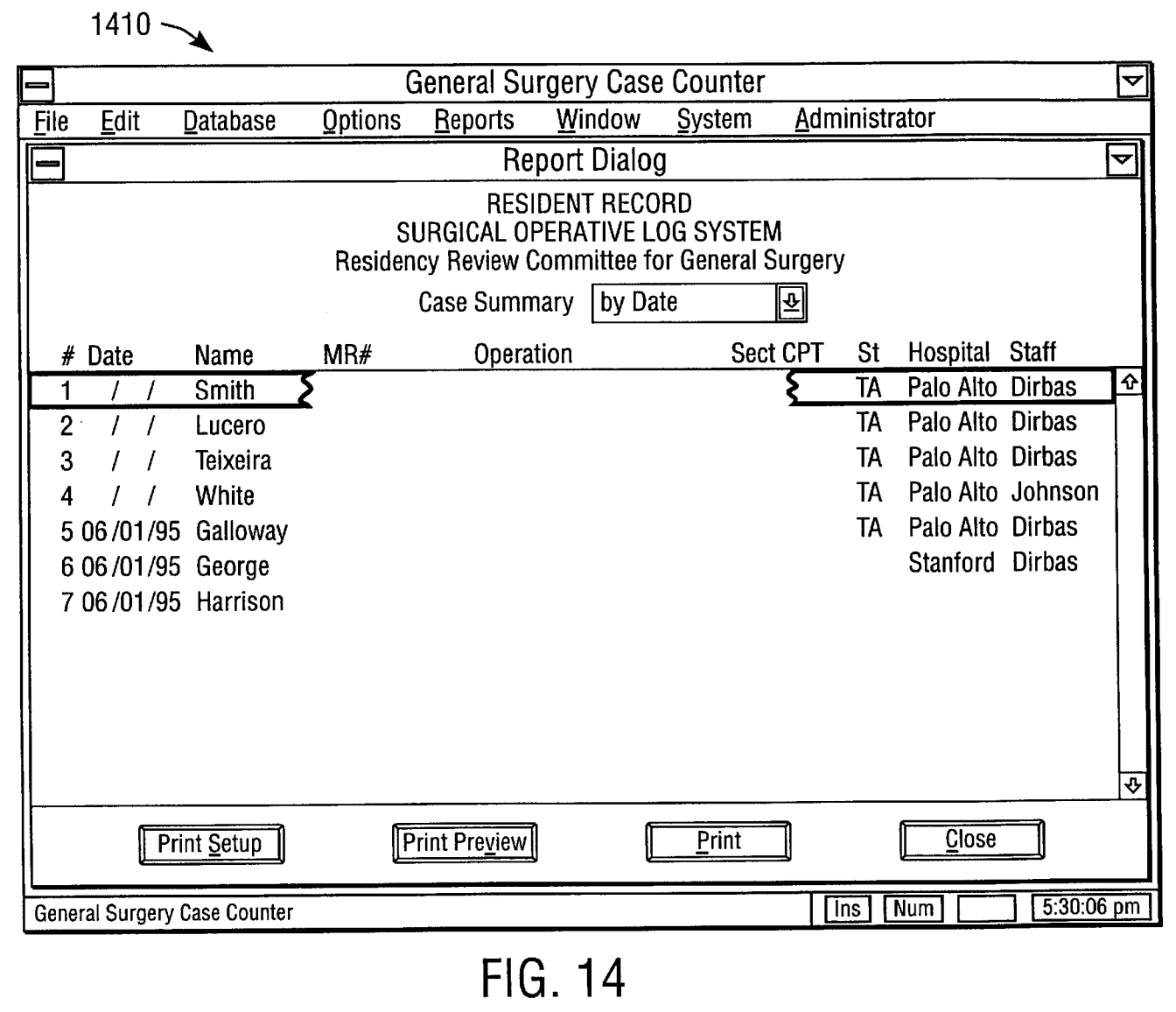

FIG. 12 is an example of a screen display 1210 for selecting the data to include in a morbidity and mortality report, which is generated by Quality Assurance Data Screen 330 in FIG. 3. FIG. 13 is an example of a screen display 1310 for selecting the data to include in an RRC report, which is generated by RRC Report Option Screen 342 in FIG. 3. FIG. 14 is an example of a screen display 1410 of a case summary report by date, which is Case Summary Report by Date 363 in FIG. 3.

An example of pseudo-code for the present invention is included in the attached Appendix to further provide an example of how to implement the above described functionality in the preferred embodiment.

While a full and complete disclosure of the invention has been provided herein above, it will be obvious to those skilled in the art that various modifications and changes may be made.

What is claimed is:

1. In a computer system, a method of providing a medical information log system, comprising the steps of:

accepting input data, said input data comprising multiple log entries, said log entries each being associated with a medical procedure, said log entries each including information identifying at least one doctor, said log entries each including a set of classification codes, said set of classification codes comprising at least one classification code, said classification codes each defining said medical procedure by type;

storing said input data in a memory within said computer system, said input data being placed in an organized database within said computer system;

tracking said input data;

accepting upon demand a designation of desired output data, said output data comprising information from selected portions of said input data;

presenting upon demand said output data, wherein said output data comprises said information identifying at least one doctor and said set of classification codes;

wherein said set of classification codes includes an RRC code; and wherein at least one of said log entries includes an override code for converting said RRC code into a CPT code, said override code replacing a default RRC-to-CPT mapping.

2. In a computer system, a method of providing a medical information log system, comprising the steps of:

accepting input data, said input data comprising multiple log entries, said log entries each being associated with a medical procedure, said log entries each including information identifying at least one doctor, said log entries each including a set of classification codes, said set of classification codes comprising at least one classification code, said classification codes each defining said medical procedure by type;

storing said input data in a memory within said computer system, said input data being placed in an organized database within said computer system;

tracking said input data;

accepting upon demand a designation of desired output data, said output data comprising information from selected portions of said input data; and presenting upon demand said output data, wherein said output data comprises said information identifying at least one doctor and said set of classification codes;

wherein a particular classification code from said set of classification codes is accepted within said data accepting step using a method comprising the steps of accepting a set of variables describing candidate codes, said set of variables comprising at least one variable;

displaying a list of candidate codes consistent with said set of variables;

accepting a candidate code from said list as said particular classification code;

wherein said set of variables comprises a category classification, and wherein said code is an RRC code.

3. In a computer system, a method of providing a medical information log system, comprising the steps of:

accepting input data, said input data comprising multiple log entries, said log entries each being associated with a medical procedure, said log entries each including information identifying at least one doctor, said log entries each including a set of classification codes, said set of classification codes comprising at least one classification code, said classification codes each defining said medical procedure by type;

storing said input data in a memory within said computer system, said input data being placed in an organized database within said computer system;

tracking said input data;

accepting upon demand a designation of desired output data, said output data comprising information from selected portions of said input data;

presenting upon demand said output data, wherein said output data comprises said information identifying at least one doctor and said set of classification codes; and wherein a particular classification code from said set of classification codes is accepted within said data accepting step using a method comprising the steps:

accepting a range specification of candidate codes;

displaying a list of candidate codes within said range specification; and accepting a candidate code from said list as said particular classification code.

4. A computer system for providing a medical information log system, comprising:

a computer processor;

an input device coupled to said processor;

an output device coupled to said processor;

a first input user interface operative on said processor, said first user input interface for accepting input data, said input data comprising multiple log entries, said log entries each being associated with a medical procedure, said log entries each including information identifying at least one doctor, said log entries each including a set of classification codes, said set of classification codes comprising at least one classification code, said classification codes each defining said medical procedure by type, wherein the medical information log system permits review of said data by said information identifying at least one doctor and said classification codes;

a memory coupled to said processor, said memory for storing said input data, said input data being placed in an organized database within said memory;

a database engine operative on said processor for tracking said input data within said database;

a second input user interface operative on said processor, said second input user interface for accepting a designation of desired output data, said output data comprising information from selected portions of said input data;

an output user interface operative on said processor, said output user interface for presenting said output data;

wherein said first input user interface accepts a particular classification code within said set of classification codes by accepting a set of variables describing candidate codes, said set of variables comprising at least one variable; displaying a list of candidate codes consistent with said set of variables; and accepting a candidate code from said list as said particular classification code; and wherein said set of variables comprises a category classification, and wherein said code is an RRC code.

5. A computer system for providing a medical information log system, comprising:

a computer processor;

an input device coupled to said processor;

an output device coupled to said processor;

a first input user interface operative on said processor, said first user input interface for accepting input data, said input data comprising multiple log entries, said log entries each being associated with a medical procedure, said log entries each including information identifying at least one doctor, said log entries each including a set of classification codes, said set of classification codes comprising at least one classification code, said classification codes each defining said medical procedure by type, wherein the medical information log system permits review of said data by said information identifying at least one doctor and said classification codes;

a memory coupled to said processor, said memory for storing said input data, said input data being placed in an organized database within said memory;

a database engine operative on said processor for tracking said input data within said database;

a second input user interface operative on said processor, said second input user interface for accepting a designation of desired output data, said output data comprising information from selected portions of said input data;

an output user interface operative on said processor, said output user interface for presenting said output data;

wherein said set of classification codes includes an RRC code; and wherein at least one of said log entries includes an override code for converting said RRC code into a CPT code, said override code replacing a default RRC-to-CPT mapping.

* * * * *